United States Patent [19]

Proctor

[11] Patent Number: 5,352,442
[45] Date of Patent: Oct. 4, 1994

[54] TOPICAL TEMPO

[76] Inventor: Peter H. Proctor, 4126 Southwest Freeway, Suite 1616, Houston, Tex. 77027

[21] Appl. No.: 21,970

[22] Filed: Feb. 24, 1993

Related U.S. Application Data

[63] Continuation-in-part of Ser. No. 149,720, Jan. 29, 1988, abandoned, which is a continuation-in-part of Ser. No. 8,186, Jan. 28, 1987, abandoned, which is a continuation-in-part of Ser. No. 858,050, Apr. 30, 1986, abandoned, which is a continuation-in-part of Ser. No. 757,131, Jul. 18, 1985, abandoned.

[51] Int. Cl.$^5$ .................. A61K 7/06; A61K 31/47
[52] U.S. Cl. .................... 424/70; 514/309; 514/310; 546/192
[58] Field of Search .......... 514/309, 310; 424/70; 546/192

[56] References Cited

U.S. PATENT DOCUMENTS

| | | | |
|---|---|---|---|
| 2,409,754 | 10/1946 | Henze | 260/309.5 |
| 2,986,573 | 5/1961 | Topliss | 167/65 |
| 3,257,390 | 6/1966 | Patchett | 260/239.55 |
| 3,461,461 | 8/1969 | Anthony et al. | 260/256.4 |
| 3,527,864 | 9/1970 | MacMillen et al. | 424/177 |
| 3,551,554 | 12/1970 | Herschler | 424/7.1 |
| 3,896,238 | 7/1975 | Smith | 424/358 |
| 4,139,619 | 2/1979 | Chidsey, III | 424/45 |
| 4,189,039 | 1/1980 | Soldati | 544/12 |
| 4,254,145 | 3/1981 | Birnbaum | 424/305 |
| 4,327,245 | 8/1982 | Shapiro | 424/241 |
| 4,344,941 | 8/1982 | Wiechert | 424/243 |
| 4,367,227 | 1/1983 | Bingham | 424/243 |
| 4,444,762 | 4/1984 | Rajadhyaksha | 424/180 |
| 4,456,600 | 6/1984 | Wiechert | 424/238 |
| 4,488,901 | 12/1984 | Farkas et al. | 71/121 |
| 4,596,812 | 6/1986 | Chidsey, III | 514/256 |
| 4,866,067 | 9/1989 | DiSchiena | 514/275 |

FOREIGN PATENT DOCUMENTS

| | | |
|---|---|---|
| 0415598 | of 0000 | European Pat. Off. . |
| 0027655 | 4/1981 | European Pat. Off. . |
| 0273202 | 7/1988 | European Pat. Off. . |
| 0327263 | 8/1989 | European Pat. Off. . |
| 2198132 | 6/1988 | United Kingdom . |
| 8302558 | 8/1983 | World Int. Prop. O. . |
| 8600616 | 1/1986 | World Int. Prop. O. . |
| 8700427 | 1/1987 | World Int. Prop. O. . |

OTHER PUBLICATIONS

Anderson, *Chemical Abstracts*, vol. 90, p. 311K (1979).
Ando et al., *Chemical Abstracts*, 93:79872n (1980).
Bazzano et al., *Journal of American Academy of Dermatology*, vol. 15, pp. 880-883 (1986).
Barry, *Pharmacology of the Skin*, vol. 1, pp. 121-137 (1987).
Cheng et al., *Archives of Dermatological Research*, vol. 278, pp. 470-473 (1986).
Cumming et al., *Journal of American Medical Association*, vol. 247, pp. 1295-1298 (1982).
Dawber, *Dermatologica*, vol. 175, suppl. 2, pp. 23-28 (1987).
DeVillez, *Archives of Dermatology*, vol. 121, pp. 197-202, (1985).
Dostert et al., *Xenobiotica*, vol. 15, No. 10, pp. 799-803 (1985).
Ehman et al., *Investigative Radiology*, vol. 21, pp. 125-131 (1986).
Feelisch et al., *Evr. Journal of Pharmacology*, vol. 139, pp. 19-30 (1987).
Feelisch et al., *Evr. Journal of Pharmacology*, vol. 142, pp. 405-409 (1987).
Fox et al., *Annals of the New York Academy of Sciences*, vol. 411, pp. 14-19 (1983).

(List continued on next page.)

*Primary Examiner*—José G. Dees
*Assistant Examiner*—Porfirio Nazario-Gonzalez
*Attorney, Agent, or Firm*—Daniel N. Lundeen; Andrew S. Pryzant

[57] ABSTRACT

Topical 2,2,6,6-tetramethyl-1-piperdinyloxyl (TEMPO) is disclosed. The compound has utility in a topical pharmaceutical formulation for the cosmetic treatment of hair loss and the cosmetic stimulation of hair growth.

10 Claims, No Drawings

OTHER PUBLICATIONS

Goffman et al., *International Journal of Radiation, Oncology, Biology and Physics*, vol. 22, pp. 803–806 (Nov. 4, 1992).

Headington, *Current Therapeutic Research*, vol. 36, pp. 1098–1105 (1984).

Hearse et al., *Circulation Research*, vol. 60, pp. 375–383 (1987).

Ignarro et al., *Biochemica et. Biophysica Acta*, vol. 631, pp. 221–231 (1980).

Karlsson et al., *Journal of Cyclic Nucleotide and Protein Res.*, vol. 10, No. 4, pp. 309–315 (1985).

Kvedar, *Journal of American Academic Dermatology*, vol. 12, pp. 215–225 (1985).

*Longevity*, vol. 2, No. 3, p. 26 (Jan. 1988).

Lucky, *Archives of Dermatology*, vol. 121, pp. 57–62 (1985).

Messina, *Current Therapeutic Research*, vol. 34, pp. 319–324 (1983).

Messina, *Current Therapeutic Research*, vol. 38, pp. 269–282 (1985).

Mittal et al., *Proc. of National Academy of Science*, USA, vol. 74, No. 10, pp. 4360–4364 (1977).

Palmer et al., *Nature*, vol. 327, pp. 524–526 (Jun. 11, 1987).

Parrett et al., *Journal of Pharmacology*, vol. 91, pp. 49–59 (1987).

Proctor et al., *Physiological Chemistry and Physics in Medical NMR*, vol. 16, pp. 175–195 (1984).

Ross, U.S. Department of Commerce, National Bureau of Standards, *Publication NSRDS-NBS59* (Jan. 1977).

Shapiro et al., *Journal of Clinical Endocrinology and Metabolism*, vol. 51, pp. 429–430 (1980).

Stewart, *International Journal of Dermatology*, vol. 17, pp. 167–179 (1978).

Thompson, *Federal Drug Administration Consumer*, pp. 10 and 12 (Mar. 10, 1981).

Tiffany-Castiglion, *Biochemical Pharmacology*, vol. 31, No. 2, pp. 181–188 (1982).

Vermorken, *Acta Dermatovener* (Stockholm), vol. 63, pp. 268–269 (1982).

Watanabe et al., *Archives of Dermatological Research*, vol. 278, pp. 470–473 (1986).

Weissmann, *Archives of Dermatology*, vol. 121, pp. 57–62 (1985).

Yoshioka et al., *Archives of Dermatological Research*, vol. 278, pp. 177–183 (1986).

*Current Therapy*, pp. 599–603 (1984).

Dahl, *Men's Fitness*, pp. 93–95 (Feb. 1989).

*Dermatologica*, vol. 175, suppl. 2, pp. 1–56 (Oct. 87).

Fiedler, *Dermatologica*, vol. 175, suppl. 2, pp. 29–35 (1987).

Mitchell et al., IBC USA Conference, South Natick, Mass. (Jun. 27, 1991).

*Physician's Desk Reference*, pp. 883, 977–978, 1782–1785, 1961 (1983).

Sekura, *Advances of Biology and Skin*, vol. XII, pp. 257–269, (1972).

Torre (Ed.), *Annals of the New York Academy of Sciences*, vol. 411, Table of Contents (1983).

Voorhees (Ed.), *Dermatologica*, vol. 175, suppl. 2, pp. 1–56 (1987).

Chemical Abstracts, vol. 96, No. 8, Chem. Abs. No. 61950p, 1981.

Herschler, *Chemical Abstracts*, vol. 78, pp. 115–239 (1973).

*Journal of American Medical Association*, vol. 260, No. 20 (1988).

TOPICAL TEMPO

CROSS-REFERENCE TO RELATED APPLICATIONS

This application is a continuation-in-part of copending application Ser. No. 07/149,720, filed Jan. 29, 1988, abandoned; which is a continuation-in-part of application Ser. No. 07/008,186, Jan. 28, 1987, abandoned; which is a continuation-in-part of application Ser. No. 06/858,050, Apr. 30, 1986, abandoned; which is a continuation-in-part of application Ser. No. 06/757,131, Jul. 18, 1985, abandoned.

FIELD OF THE INVENTION

This invention relates to topical 2,2,6,6-tetramethyl-1-piperidinyloxyl (TEMPO), and the treatment of hair loss therewith.

BACKGROUND OF THE INVENTION

Recently, several anti-alopecia agents such as minoxidil and cyoctol have gained attention. However, most of these anti-alopecia agents are only minimally effective in some cases and/or can cause adverse dermatological or systemic reactions. Thus, the search continues for new, safer and more effective anti-alopecia agents.

SUMMARY OF THE INVENTION

Applicant has discovered that 2,2,6,6-tetramethyl-1-piperidinyloxyl (TEMPO) can be used as a topical anti-alopecia agent, for example, to stimulate cosmetic hair growth.

DETAILED DESCRIPTION OF THE INVENTION

In the present invention, 2,2,6,6-tetramethyl-1-piperidinyioxyl (TEMPO) is compounded in a topical formulation. The pharmaceutical carrier, in which the TEMPO is generally substantially homogeneously dispersed can be an aqueous dispersion or suspension, or a water-in-oil or oil-in-water emulsion. Pharmaceutical carriers which can be mentioned include water, urea, alcohols and glycols such as methanol, ethanol, propanol, butanol, ethylene glycol, propylene glycol, and the like.

Suitable water-in-oil emulsions are commercially available under the designations Aquaphor, cold cream, Eucerin, hydrous lanolin, Hydrosorb hydrophilic petrolatum, Nivea, Polysorb, Qualatum and Velvachol. Suitable oil-in-water emulsions are available commercially under the designations acid mantle cream, Almay emulsion cream, Cetaphil, Dermabase, Dermavan, hydrophilic ointment, Keri cream, Lubriderm cream, Multibase cream, Neobase cream, Unibase cream, Vanibase cream and Wibi. The carrier may further contain various other emollients, emulsifiers, water, perfumes, colorants, preservatives, and the like. The topical formulation is in the form of a cream, lotion, shampoo, cream rinse, or the like.

TEMPO is a stable nitroxide radical which is a commercially available spin label. TEMPO can be substituted, typically in the 4 position, for example, 4-amino, 4-(2-bromoacetamido), 4-(ethoxyfluorophosphonyloxy), 4-hydroxy, 4-(2-iodoacetamido), 4-isothiocyanato, 4-maleimido, 4-(4-nitrobenzoyloxyl), 4-oxo, 4-phosphonooxy, and the like.

Effective amounts of the TEMPO generally range from about 0.01 to about 20% by weight of the topical composition, more preferably from about 0.1 to about 10% by weight, most preferably from about 0.5 to about 3% by weight, but more or less can be present in the composition depending on the particular TEMPO formulation and the treatment conditions.

The topical TEMPO can be used alone or in combination with other hair growth stimulants or additaments which are available to enhance the function of the hair growth stimulant, such as, for example, the hydroxyl radical scavengers, antiandrogens and others described in International Publication No. WO 87/00427 (International Application No. PCT/US86/01393) published on Jan, 29, 1987; and European Patent Application No. 89300785.6, Publication No. 0327263/A1, published Aug. 9, 1989; both of which are hereby incorporated in their entirety herein as though fully set forth verbatim, including reference therein to the publication of Ross & Ross, "Selected Specific Rates of Reactions of Transients From Water In Aqueous Solution. III. Hydroxyl Radical and Pure Hydroxyl Radicals and Their Radical Ions," National Standard Reference Data Series, National Bureau of Standards, 59 (1977), which is also incorporated herein by reference.

According to the present invention, the topical TEMPO is applied to the skin to be treated, such as the scalp. Depending on the type of hair loss or alopecia being treated and the conditions thereof, the stimulation of hair growth can usually be obtained by topical application, preferably repeated daily application for a period of 3–6 months. The utility of topical TEMPO is not limited thereto, however, and the stimulation of hair growth can include an increased rate of growth, increased hair diameter, follicular neogenesis, and the like, as well as inhibiting hair loss or alopecia from progressing, for example, in male pattern baldness, or during the course of treatment with other therapeutic agents known to induce hair loss, such as chemotherapy or radiation therapy in cancer treatment. The topical TEMPO can, if desired, be essentially free of minoxidil for use by individuals sensitive to minoxidil.

The invention is illustrated by way of the following examples:

EXAMPLE 1

A TEMPO shampoo is prepared by mixing 0.5 g of 4-hydroxy-TEMPO in 500 ml of a commercially available shampoo. The shampoo is used daily on the scalp for normal shampooing of the hair for a period of from 3 to 6 months to obtain cosmetic hair growth.

EXAMPLE 2

A solution of TEMPO is prepared and used in the course of radiation treatment. 4-Hydroxy-TEMPO, obtained commercially from Aldrich Chemical Company, is dissolved in 70 percent ethanol/30 percent water at a concentration of 70 mg/mi. Topical application of the solution is made prior to irradiation exposure at 20 Gy to 50 Gy. Hair loss in the treated TEMPO subjects is less severe and returns to normal more rapidly than in the control group similarly treated with the same ethanol/water solution without TEMPO. Skin samples obtained from the treated group test positive for the presence of 4-hydroxy-TEMPO, while other tissue and blood specimens generally test negative. The application of the solution can also continue daily after the irradiation exposure. See Goffman, et al., "Topical Application of Nitroxide Protects Radiation-Induced Alopecia in Guinea Pigs," International Journal of Radiation Oncology, Biology and Physics, Volume 22, pp. 803–806, 1992, which is hereby incorporated herein by reference.

The invention is described above and illustrated herein with reference to specific chemical formulas, preparations and therapeutic and cosmetic applications. Many variations and modifications will become apparent to those skilled in the art in view of the foregoing disclosure. It is intended that the following claims are not to be limited thereby, and are to be construed in accordance with the spirit and scope thereof.

I claim:

1. Topical 2,2,6,6-tetramethyl-1-piperidinyloxyl having utility in the treatment of hair loss from radiation, comprising a dispersion, suspension or emulsion selected from creams, lotions, shampoos and cream rinses.

2. 2,2,6,6-Tetramethyl-1-piperidinyloxyl in a topical pharmaceutical carrier, comprising a dispersion, suspension or emulsion selected from creams, lotions, shampoos and cream rinses, in an amount effective to treat radiation-induced alopecia.

3. Topical 4-hydroxy-2,2,6,6-tetramethyl-1-piperidinyloxyl having utility in the treatment of hair loss from radiation, comprising a dispersion, suspension or emulsion selected from creams, lotions, shampoos and cream rinses.

4. 2,2,6,6-Tetramethyl-1-piperidinyl-1-oxyl in a topical pharmaceutical carrier for the treatment of hair loss from radiation, comprising a dispersion, suspension or emulsion selected from creams, lotions, shampoos and cream rinses, including a substituent selected from:
   4-amino;
   4-(2-bromoacetamideo);
   4-(ethoxyfluorophosphonyloxy);
   4-hydroxy;
   4-(2-iodacetamido);
   4-maleimido;
   4-(4-nitrobenzoyloxy);
   4-oxo; and
   4-phosphonooxy.

5. The composition of claim 2 comprising from about 0.01 to about 20 percent by weight of said piperidinyloxyl.

6. A topical dispersion, suspension or emulsion selected from creams, lotions, shampoos and cream rinses, comprising an effective amount from about 0.01 to about 20 percent by weight of a 4-substituted piperidine N-oxide for the stimulation of hair growth in the treatment of radiation-induced alopecia by repeated topical application having the formula:

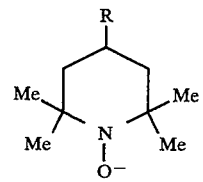

wherein R is selected from hydroxyl; amino; 2-bromoacetamideo; ethoxyfluorophosphonyloxy; iodoacetamido; isothiocyanato; maleimido; 4-nitrobenzoyloxyl; oxo; and phosphonooxy.

7. The preparation of claim 6, wherein R is hydroxy and the substituted piperidine N-oxide is present in the preparation at from about 0.5 to about 3 percent by weight.

8. The composition of claim 1, comprising from about 0.01 to about 20 percent by weight of said piperidinyloxyl.

9. The composition of claim 3 comprising from about 0.01 to about 20 percent by weight of said piperidinyloxyl.

10. The composition of claim 4 comprising from about 0.01 to about 20 percent by weight of said piperidinyloxyl.

* * * * *

UNITED STATES PATENT AND TRADEMARK OFFICE
CERTIFICATE OF CORRECTION

PATENT NO. : 5,352,442
DATED : October 4, 1994
INVENTOR(S) : Peter H. Proctor

It is certified that error appears in the above-indentified patent and that said Letters Patent is hereby corrected as shown below:

At col. 1, line 39, "piperidinyioxyl" should read "piperidinyloxyl".
At col. 2, line 58, "mg/mi" should read "mg/ml".
At col. 3, line 36, "4-(2-bromoacetamideo)" should read "4-(2-bromoacetamido)".
At col. 3, line 39, "4-(2-iodacetamido)" should read "4-(2-iodoacetamido)".
At col. 4, line 1, "4-(4-nitrobenzoyloxy)" should read "4-(4-nitrobenzoyloxyl)".

UNITED STATES PATENT AND TRADEMARK OFFICE
CERTIFICATE OF CORRECTION

PATENT NO. : 5,352,442
DATED : October 4, 1994
INVENTOR(S) : Peter H. Proctor

It is certified that error appears in the above-indentified patent and that said Letters Patent is hereby corrected as shown below:

At col. 4, in the chemical structure between lines 15-22:

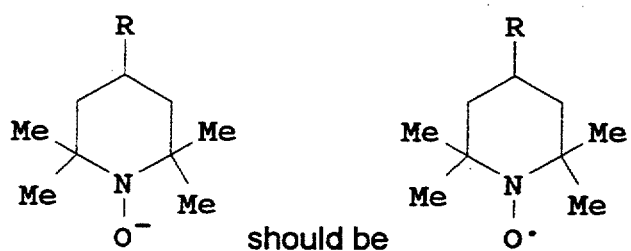

At col. 4, lines 23-24, "2-bromoacetamideo" should read "2-bromoacetamido".

Signed and Sealed this

Tenth Day of January, 1995

*Attest:*

BRUCE LEHMAN

*Attesting Officer*   Commissioner of Patents and Trademarks